United States Patent [19]
Bishop et al.

[11] Patent Number: 5,328,827
[45] Date of Patent: Jul. 12, 1994

[54] SPECIFIC DNA MOLECULAR PROBES FOR BOS-TYPE MALE GENOME

[75] Inventors: Colin Bishop, Neuilly-sur-Seine; Corinne Cotinot, Villejuif; Marc Fellous, Paris; Marek Kirszenbaum, Jouy-en-Josas; Marcel Vaiman, Paris, all of France

[73] Assignees: Institut National de la Recherche Agronomique - INRA; Institut Pasteur; Commissariat a l'Energie Atomique, all of Paris, France

[21] Appl. No.: 995,932

[22] Filed: Dec. 28, 1992

Related U.S. Application Data

[63] Continuation of Ser. No. 477,855, Apr. 24, 1990, abandoned.

[30] Foreign Application Priority Data

Aug. 27, 1987 [FR] France .................. 87 11975

[51] Int. Cl.$^5$ .................. C12Q 1/68; C12P 19/34; C07H 21/04; C07H 21/02
[52] U.S. Cl. .................. 435/6; 435/91.1; 435/91.2; 536/18.7; 536/23.1; 536/24.31; 536/24.33; 935/19; 935/77; 935/78.1; 935/70
[58] Field of Search .............. 435/6, 172.3, 501, 374, 435/91.1, 91.2; 536/23.1, 24.3, 24.33, 18.7, 24.31; 935/3, 9, 63, 78

[56] References Cited

U.S. PATENT DOCUMENTS

| | | | |
|---|---|---|---|
| 4,683,195 | 7/1987 | Mullis | 435/6 |
| 4,769,319 | 9/1988 | Ellis et al. | 435/6 |
| 4,960,690 | 10/1990 | Ellis et al. | 435/6 |
| 5,055,393 | 10/1991 | Kwoh et al. | 435/6 |

FOREIGN PATENT DOCUMENTS

| | | |
|---|---|---|
| 0204510 | 12/1986 | European Pat. Off. . |
| 0235046 | 9/1987 | European Pat. Off. . |
| 2476321 | 8/1980 | France . |
| 8600342 | 1/1986 | World Int. Prop. O. . |
| 8607095 | 12/1986 | World Int. Prop. O. . |

OTHER PUBLICATIONS

Cold Spring Harbor Symposia on Quantitative Biology, vol. 51, No. "mol. biol". 1986, Cold Spring Harbor Laboratory, (U.S.), K. Mullis et al.: Specific Enzymatic Amplification of DNA In Vitro: The Polymerase Chain Reaction, pp. 263–273.
Biology of Reproduction, vol. 30, Supplement 1, 1984, K. A. Lakoski et al.: "Development of the Acrosome: Sperm Antigens Involved in Fertilization Probed with Monoclonal Antibodies", p. 134.
Theriogenology, vol. 27, No. 1, Jan. 1987, M. Leonard et al.: "Sexing Bovine Embryos Using Y Chromosome Specific DNA Probe", p. 248.
Cytogenetics and Cell Genetics, vol. 46, No. 1–4, 1987, (Cho, C. Cotinot, et al.: "Cloning and Characterization of Bovine Y Derived Sequences", p. 598.
Streeck, Nature, 298:767–69 (1982).
Burk et al., Mol. Cell. Biol., 5(3):576–81 (1985).
Nalleseth et al., Mol Gen. Genet., 190:80–84 (1983).
Lamar et al., Cell, 37:171–77 (1984).
Pech et al., Cell, 18:883–93 (1979).
Bishop et al., Nature, 303(30):831–2 (1983).
Gosden et al., The Lancet, 540–541 (1984).
Burns et al., J. Clin. Pathol., 38:1085–92 (1985).
Lau et al., The Lancet, 5:14–15 (1984).
Vergnaud et al., Brit. Med. J., 289:73–76 (1984).
Kunkel et al., Science, 191:1189–90 (1976).
Bostock et al., Nature, 272:324–28 (1978).

Primary Examiner—Margaret Parr
Assistant Examiner—Miguel J. Escallon
Attorney, Agent, or Firm—Oblon, Spivak, McClelland, Maier & Neustadt

[57] ABSTRACT

Synthetic oligonucleotides of 17 or more consecutive nucleotides of the 49 bases of formula (A) to be used as molecular probes for sexing the embryos or foetuses of ruminant mammals or as molecular probes for detecting a Y chromosome in a spermatozoid population of ruminant mammals of the Bos genus and their use in process of amplification and hybridization assays.

6 Claims, No Drawings

SPECIFIC DNA MOLECULAR PROBES FOR BOS-TYPE MALE GENOME

This application is a continuation of application Ser. No. 07/477,855, filed on Apr. 24, 1990, now abandoned.

The present invention relates to specific DNA molecular probes useful for the determination of the sex—or sexing—of ruminant embryos or foeti, particularly of the sub-family of bovines, and in particular of the bos genus, having DNA sequences specific of the male sex, as well as to flanking or primer sequences for the genetic amplification of these probes; the present invention also encompasses the applications of said probes preferably amplified by means of the above-said flanking sequences, and particularly their applications to the determination of the sex of embryos and of foeti of the above-said ruminants, and for checking the presence of the Y chromosome in a spermatozoa population as well as to the separation of said population into two groups comprising respectively to the Y chromosome and the X chromosome, for artificial insemination.

The international application PCT 86/07095 in the name of THE SALK INSTITUTE BIOTECHNOLOGY INDUSTRIAL ASSOCIATES, filed 30 May 1986 claiming a priority U.S. Ser. No. 739 817 of 31 May 1985 and published 4 Dec. 1986, describes nucleic acid probes for the pre-natal sexing of males of the Bos genus, more particularly of the Hereford and Holstein breeds. These probes which have the characteristic of being formed of nucleic acids which hybridize significantly with the total DNA of males of one of the aforesaid breeds of the Bos genus, comprise:

a) Either a segment which has substantially the same sequence as:
   the smallest PstI fragment of the plasmid pES5 (2),
   or the smallest fragment PstI of the plasmid PES8,
   or the 6.2 kbp EcoRI fragment of the genome of lambda-ES6.0;
b) or any segment greater than length of 20 bp of anyone of the segments enumerated under a);
c) or either of the strands of one of the segments enumerated under a) and b);
d) or the single or double stranded RNA, having the same sequence as one of the segments enumerated under a), b) and c) above.

However, although the RNA is mentioned in this PCT International Application (see d) above), it seems that the preferred nucleic acids are the DNA and are constituted by the EcoRI fragment of 6.2 kbp, 4.0 kbp or 2.2. kbp of the genome of the lambda-ES6.0.

In accordance with this International Application, the method of sexing embryos or foeti of the Bos genus consists of:

placing in contact the DNA of cells of the embryo or of the foetus, in hybridization conditions, with one or several hybridization probes as defined above, each labelled detectably;
verifying a significant hybridization is produced between the DNA of the cells of the embryo or of the foetus and the one or more hybridization probes.

According to the PCT International Application concerned, the hybridization probes are obtained by nick-translation and the embryo or foetus DNA would only come from at least 4, but preferably from at least 10, embryo cells.

The PCT International Application 86/07095 describes in addition a method for isolating a DNA clone coming from a genome bank of the males of the species concerned, which consists of:

screening the genomic library by hybridization of nucleic acids with a male-specific probe comprising the total male DNA and the total female DNA of the species, to identify the clones of the library which comprise the DNA which hybridizes with a fragment containing a male specific DNA segment said screening being performed on a solid support pre-hybridized with the total female DNA of the species, fragmented randomly to have an average length of about 20 or 1000 nucleotides;
then identifying the clones of the library identified in the course of the screening, which shelter the DNA which hybridizes considerably more with the total male DNA of the species than with the total female DNA of said species.

In practice, to permit detectable hybridization with the small amounts of embryonic DNA available in the small number of cells which can be taken out from the embryos or foeti to be sexed, it is preferred for the nucleic acids used as probes to be labelled with radioactive atoms and it seems also preferable to use conjointly two of the above defined probes.

Three male-specific probes were obtained, of which the first corresponds to the RsAI fragment of 5–6 kbp of male bovine DNA, the second to the RsaI-EcoRI fragment of 4 kbp of male bovine DNA and the third to the EcoRI fragment of 2.2 kbp of male bovine DNA, and their sequence in nucleotides has been at least in part identified.

However, due to their length itself, it is difficult to envisage synthesizing such probes, of which nothing indicates, after all, in said PCT International Application, what are the segments of these sequencies which are "specifically" male-specific and are in fact useful for the sexing of embryos, and which have manifestly not been identified.

Applicants have, on their side, isolated a specific DNA molecular probe of DNA specific male genome of mammals, particularly of the Bos genus—which the Inventors have besides succeeded in synthetizing—, of which the hybridization profile (determined by hybridization of said probe with the male genomic DNA digested with EcoRI) shows the presence of a band of the order of 7 kb specific for the male genome of the Bos genus (and absent from the female genomic DNA), which probe—which has received the name bc.1.2.—comprises 49 pairs of bases whose sequence in nucleotides (A) is as follows:

5'—ATCAGTGCAGGGACCGAGATGTGCTCCAAGGAGTGTTTATCGGCTGCTT—3' (A)

or a fragment of said sequence comprising at least 11 nucleotides.

This probe is described and claimed in a Patent Application filed in France in the name of the Applicants on the date of 28 Feb. 1986, under no. 86 02811, and its applications are described and claimed, on the one hand, in said application, and, on the other hand, in a Certificate of Addition to this application, which was filed in France on 9 Sep. 1986, under no. 86 12616.

Within the compass of pursuing their research with the object of stating whether the specificity of the recognition of the male genome could be identified in a segment of the sequence of 49 nucleotides which constitutes the probe according to French Patent Application no. 86 02811, the Inventors have established that within this sequence, segments or fragments of several consecutive nucleotides show the hybridization profile defined in their Patent Application of February 1986 and are specific to the male genome of the Bos genus. The possibility of having available a probe comprising a sequence of nucleotides of short-length has considerable interest, since it permits the synthesis at will, at industrially acceptable cost prices, of such a probe which, through this fact, is completely pure and does not cause background noises.

In addition, the Inventors have succeeded in identifying the flanking segments of said probes, which has permitted them to amplify the latter and has the consequence of increasing their sensitivity, of ensuring a reliability in the determination of the sex of embryos of the order of 100 %, and of reducing the time necessary for such a determination.

Moreover, the Inventors have been able to establish that the segments or fragments of DNA of short-length which are male-specific, that they have identified and synthetized can play the role both of probes and of flanking segments, or primers.

It is an object of the present invention to provide synthetic oligo-nucleotides which are characterized in that they are constituted by fragments of a molecular probe comprising a sequence of nucleotides of 49 pairs of bases, of the Formula A, below:

(A)

known in itself, and constituting a DNA segment specific of the male genome of ruminant mammals, particularly of the Bos genus, which fragments are themselves characterized in that they comprise at least 10 bases of said sequence (A), among which are at least 5 consecutive bases of the latter, as well as their complementary fragments or any fragment having at least 60% homology with said oligo-nucleotides. According to an advantageous embodiment of the invention, the synthetic oligo-nucleotides according to the invention are characterized in that they are constituted by fragments of the molecular probe (A) which comprise 17 bases, among which are at least 5 consecutive bases of the latter and in that they correspond to formulae (1) to (8) below:

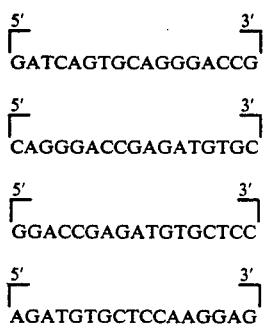

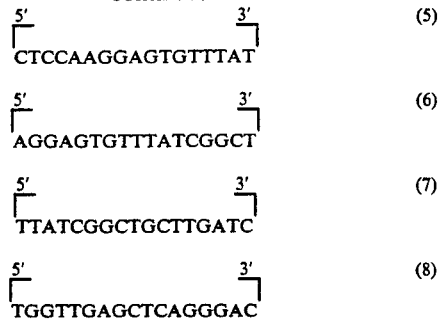

as well as their complementary fragments or any fragment having at least 60% homology with said oligo-nucleotides. In another advantageous embodiment of the invention, the synthetic oligo-nucleotides according to the invention are characterized in that they are constituted by fragments of the molecular probe (A) which comprise 20 bases each and have the sequences of nucleotides shown by formulae (9) to (11), below:

as well as their complementary fragments or a fragment of said sequences comprising at least 5 consecutive nucleotides or any fragment having at least 60% homology with said sequences.

It is emphasized that the sequence (9) corresponds to a fragment of the probe of 49 bp of formula (A) which extends from base 1 to base 20, that sequence (10) corresponds to a fragment of the probe of 49 bp formula (A) which extends from base 21 to base 40 and that the sequence (11) corresponds to a fragment of said probe which extends from the base 11 to base 30.

The International PCT Application no. 86/07095 in the name of THE SALK INSTITUTE BIOTECHNOLOGY INDUSTRIAL ASSOCIATES INC. (abbreviated "SIBIA") filed on 30 May 1986 claiming the priority of an initial application of 31 May 1985 in the United States, described, as indicated above, the partial sequence of total (chromosomic) DNA extracted from bovine cells and particularly describes sequences constituting respectively the RsaI fragment of 5–6 kbp and the EcoRI fragment of 4 kbp the bovine male DNA and this application has given the partial sequence comprising these two fragments.

The Inventors have, on their side, synthetized a certain number of fragments of the bovine DNA sequence and have been able to establish that these fragments on the one hand, are male-specific, and are suitable for constituting molecular probes for the sexing, of embryos, and on the other hand, are suitable to play the part of primers or flanking segments and, consequently, to amplify the fragments of the DNA sequence which play the part of the probes, particularly the molecular probe (A), which is also the case of fragments (1) to (8) and (9) to (11) each of which can as just as well play the part of a primer or flanking segment of another of these fragments used as a probe, as the part of the probe amplified by each of said fragments. According to the present invention, said fragments of the bovine DNA sequence are characterized in that they have the sequences in nucleotides shown by the formulas (12) to (29) below:

```
5'                                                                      3'
ACCGGTCTAGGTCTAGCCCTTGTTCGGGACGCACATCACAGGCTCCTGAGCCCCCATCTC         (12)

5'                                                                      3'
GGTAGAGCCCGCATCTCGGTCCCCGCGGTGAACCTGGCCCGGTTCCTACCCCAGTC             (13)

5'                                                                      3'
CTGAGGCCTCCTCTCGCACTCTGCCCTGAAGCCGTGCGCGTCCTGCCCTCGATCAGACCT         (14)

5'                                                                      3'
GACAGGGTGGGCCGTGCCCTCGTTCAGTCACCCGGGAAACACTGCTGAGCCCGCATCTTG         (15)

5'                                                                      3'
ACACTGCTGAGCCCGCATCTTGATCCCCGCGCTAAACCTGGCCGGCTCCTACCCCCAGG          (16)

5'                                                                      3'
ACCGGTCTAGGTCTGGCCCTTGTTCGATTCACTCAGCACAGACTCCTGAGCCCCCATCTC        (17)

5'                                                                      3'
AGCTGTGATCCCGCAGCTCANTCCCGGCACTGAAGCCACCTCTGGGGCTTGGCCTGCTTC        (18)

5'                                                                      3'
AGAAGCAGTCTAGGGCCTGCCTTGTTCGGAATTCGGATGGATGCTGCCCTTGGGCAACAC        (19)

5'                                                                      3'
TTCGGAATTCGGATGGATGCTGCCCTTGGGCAACACCCCCACCGCCCCCAAACTCACACA       (20)

5'                                                                      3'
AGCTCAACCACGGTGGTTTCTGCCTCTGGCCAAGGCCCTCGACAATCAATCCTGAGCCCA        (21)

5'                                                                      3'
ATCTCACGCGCTGCACTAAACCACGCAGAGTTCCGCCCTTCCTGAAGTGCCCGTCTAAAG        (22)

5'                                                                      3'
ACCAGTCGAGGTCCTGCCCTTTGTGCGGGCCCCTAGCACAGACTCCCGACCCAAACCTCT        (23)

5'                                                                      3'
ACACTGCTGAGCCCGCATCTTGATCCCCGCGCTAAACCTGGCCGGGCTCCTACCCCCAGG        (24)

5'                                                                      3'
ACCGGTCTAGGTCTGGCCCTTGTTCGATTCACTCAGCACAGACTCCTGAGCCCCCATCTC        (25)

5'                                                                      3'
CCCCCCGCCCGGTGTCTGCACTGATCCAGGCTGGCTCCTGCCCTCGGTCAAGACCCTGG         (26)

5'                                                                      3'
AGCAGGCTGGCTCCTGCCTTCGTTCAAGCACCTGGCAAAGTAACCGCCGGGAGACTCCAG        (27)

5'                                                                      3'
AGCTGTGATCCCGCAGCTCACTCCCGGACTGAAGCCACCTCTGGGGCTTGGCCTGCTTC         (28)

5'                                                                      5'
AGAAGCAGTCTAGGGCCTGCCTTCTTCGATTCCCGCGACACACACTCCTGAGCCACAGCT        (29)
```

It is also an object to the present invention to provide a method of a genic amplification of a molecular probe of DNA specific of the male genome of mammals, particularly of ruminants, more particularly of the subfamily of bovines and specifically of the genus Bos, which probe has one the sequences of nucleotides of formulae (A) and (1) to (29) above, which method of amplification consists in fixing at each of the ends, respectively, of said molecular probe, a flanking sequence judiciously selected from among the DNA fragments of formulae (.1) to (29) such as defined above, by hybridization, then in applying a procedure of enzymatic extension by means of DNA polymerase, followed by a denaturation process, and in repeating the cycle hybridization-extension-denaturation, known under the name of PCR cycle, a sufficient number of times to increase the amount of the sequence constituting the starting molecular probe in an exponential proportion with respect to the number of cycles employed.

The bovine DNA fragments useful as molecular probes of DNA specific of the male genome of the mammals mentioned above, or as flanking segments of these probes, identified above, can be, as the case may require, advantageously amplified according to the present invention, and duly labelled with a radioisotope or with a suitable non-radioactive substance, are used as described in French Patent Application no. 86 02811 and/or in its Certificate of Addition no. 86 12616, for the sexing of embryos or of foeti or for checking the Presence of the Y chromosome in a spermatozoa population, or again for the separation of spermatozoa into two populations of spermatozoa bearing respectively the Y chromosome and the X chromosome for their use in artificial insemination.

It is also an object to the present invention to provide a method for the preparation of monoclonal or polyclonal antibodies by immunisation of rodent mammals with the spermatozoa fragment bearing the Y or X chromosome checked by hybridization with a bovine DNA fragment of formula (1) to (29), or a probe of formula (A), amplified by one or several primers—or flanking segments—of formulae (1) to (29).

The present invention has in addition, the object of providing specific immunological reagents recognizing antigenic determinants checked by the X or Y chromosomes which have served for obtaining said reagents and expressed at the surface of the spermatozoas, characterized in that they are constituted by antibodies obtained by employing the aforesaid method, if necessary purified.

Besides the foregoing features, the invention comprises yet other features which will emerge from the description which follows.

The invention will be better understood by means of the additional description which follows, which refers to examples of praticing the present invention.

It must however be understood, that these examples are given purely by illustration of the invention, of which they do not constitute in any way a limitation.

EXAMPLE 1

Synthesis and Purification of Synthetic Oligonucleotides of Formulas (1) to (8) According to the Invention These eight oligonucleotides of 17 pairs of bases each, comprising at least 5 consecutive bases of the molecular probe (A), which correspond respectively to the formulae (1) to (8) given below:

$$\overset{5'}{\longmapsto} \quad \overset{3'}{\longleftarrow} \quad (1)$$
GATCAGTGCAGGGACCG -continued $$\overset{5'}{\longmapsto} \quad \overset{3'}{\longleftarrow} \quad (2)$$
CAGGGACCGAGATGTGC $$\overset{5'}{\longmapsto} \quad \overset{3'}{\longleftarrow} \quad (3)$$
GGACCGAGATGTGCTCC $$\overset{5'}{\longmapsto} \quad \overset{3'}{\longleftarrow} \quad (4)$$
AGATGTGCTCCAAGGAG $$\overset{5'}{\longmapsto} \quad \overset{3'}{\longleftarrow} \quad (5)$$
CTCCAAGGAGTGTTTAT $$\overset{5'}{\longmapsto} \quad \overset{3'}{\longleftarrow} \quad (6)$$
AGGAGTGTTTATCGGCT $$\overset{5'}{\longmapsto} \quad \overset{3'}{\longleftarrow} \quad (7)$$
TTATCGGCTGCTTGATC $$\overset{5'}{\longmapsto} \quad \overset{3'}{\longleftarrow} \quad (8)$$
TGGTTGAGCTCAGGGAC are fragments of the segments of 49 bp which has the nucleotide composition (A) indicated above.

Their chemical synthesis was performed by means of an automatic synthetizor "APPLIED BIOSYSTEMS" by the solid phase phosphoramidite technique.

The reaction being 95-97% effective at each step, it was necessary to purify the final product (sub-fragments (1) to (8)) of the intermediate oligonucleotides. About 7 mg of the oligonucleotides mixture in 60 μl H₂O were separated by electrophoresis in a 20% polyacrylamide gel +8M urea at 700 V, 38 mA for 3 hours. The bands corresponding to the 17 mer are marked by means of an aluminum foil coated with silica gel, fluorescent at 254 nm (Merck).

This portion of the gel was cut off, then the DNA was eluted in 1.5 ml of 0.5M CH₃COONH₄ solution +5 mM EDTA with stirring at 37° C. for 16 hours.

The supernatant is concentrated to about 300 μl and the urea is removed by chromatography on a column 10 cm × 1 cm of Sephadex G-50 (Pharmacia) equilibrated with the 10 mM-Tris-HCl pH 7.5+1 mM EDTA buffer. The DNA thus isolated is freeze-dried and stored at −20° C.

Radioactive Labelling (³²p) of the Synthetic Fragments (1) to (8) (Monostrand)

10 to 20 pM of fragments (1) to (8) in a volume of 3 μl are added to 23 μl of the reaction mixture composed of 100 mM dithiothreitol (2.5 μl), 10 mM spermidine (2.5 μl), 500 mM Tris-HCl incubation buffer pH 7.5+100 mM MgCl₂ (2.5 μl), 100 μCi (γ-³²p) adenosine triphosphate-ATP 3000Ci/mmole (Amersham) and 20 U T4 polynucleotide kinase (Boehringer). After incubation for 30 mn at 37° C., the reaction is stopped with 2 μl 400 mM EDTA and the labelled oligonucleotide is separated from the ATP by chromatography on a column with Sephadex G-25.

Prehybridization and Hybridization

The filters or blots are prehybridized from 42° to 65° C. for 1 to 4 hours with a mixture 5×SSPE containing 0.9M-NaCl; 50 mM NaHPO₄ pH 7.4; 5 mM EDTA pH 7.4; 5×Denhart; 0.3 mg/ml of sonicated and hydrolyzed salmon sperm DNA; 0.5% sodium dodecyl sulfate. The hybridization is carried out in the same mixture. Each of the probes radiolabelled with $^{32}$p, denaturated at 100° C. for two minutes, is added to the hybridization solution at 1 to 6×10$^6$ pm/ml.

The hybridization is performed at 40° to 65° C. for at least 1 hour. After hybridization, the filters are washed in a 2×SSC buffer plus 0.5% SDS, one or twice at 45° C. for 30 minutes. The filters are then placed in a cassette equipped with "CRONEX" (DUPONT) intensifiers, placed in contact with a Kodak XAR-5 film for autoradiography for 1 to 16 hours at −70° C.

EXAMPLE 2

Synthesis and Purification of Synthetic Oligonucleotides of Formulae (9) to (11) According to the Invention These three oligonucleotides of 20 pairs of bases each which correspond respectively to the formulae (9) to (11) below:

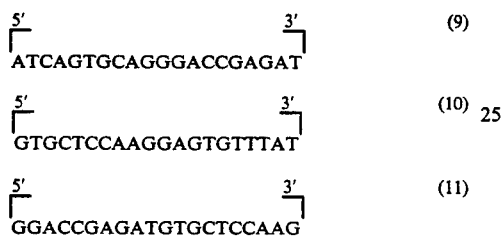

are fragments of the sequence of 49 pairs of bases of formula (A) of which sequence (9) comprises the bases 1 to 20 of the sequence (A), whilst the sequence (10) comprises the bases 21 to 40 of said sequence (A) and the sequence (11) comprises the bases 11 to 30 of said sequence (A).

The synthesis of the fragments (9) to (11) was carried out by taking the sequence (A) as a model.

This chemical synthesis was performed by means of an "Applied Biosystems" automatic synthetizor by the solid phase phosphoramidite technique.

The reaction was 95–97% effective for each probe, it was necessary to purify the final product (sub-fragments (9) to (11)-20 mer) from the intermediate oligonucleotides. About 7 mg of oligonucleotide mixture in 60 μl H$_2$O are separated by electrophoresis in the gel of 20% polyacrylamide+8M urea at 700 V, 38 mA for 3 hours. The bands corresponding to the 20 mer are marked by means of an aluminum foil coated with silica gel, fluorescent at 254 nm (Merck). This portion of the gel is cut off, then the DNA eluted in 1.5 ml of the solution 0.5M CH$_3$COONH$_4$+5mM EDTA with stirring at 37° C. for 16 hours.

The supernatant is concentrated to about 300 μl and the urea is removed by chromatography on a 10 cm×1 cm Sephadex G-50 (Pharmacia) column equilibrated with the 10 mM Tris-HCl pH 7.5+1 mM EDTA Duffer. The DNA thus isolated is freeze-dried and stored at −20° C.

Radioactive Labelling ($^{32}$p) of the (9) to (11) Synthetic Single strand) Fragments 10 to 20 pM of the (9) to (11) fragments in a volume of 3 μl are added to 23 μl of reactional mixture composed of: 100 m % dithiothrditol (2.5 μl), 10 mM spermidine (2.5 μl), incubation buffer 500 mM Tris-HCl pH 7.5+100 mM MgCl$_2$ (2.5 μl 100 μCi (−$^{32}$p) adenosine triphosphate-ATP 3000 Ci/mole (Amersham) and 20 U T4 polynucleotide kinase (Boehringer). After incubation for 30 mn at 37° C., the reaction is stopped with 2 μl 400 mM EDTA and the labelled oligonucleotide is separated from the ATP by chromatography on a column with Sephadex G-50.

Prehybridization and Hybridization

The filters or blots are prehybridized at 55° C. for 4 hours with a 5×SSPE mixture containing 0.9M NaCl; 50 mM NaHPO$_4$ pH 7.4; 5 mM EDTA PH 7.4; 5×Denhart; 0.3 mg/ml of sonicated and hybridized salmon sperm DNA; 0.5% sodium dodecyl sulfate. The hybridization is performed in the same mixture. Each of the fragments radiolabelled with $^{32}$p denaturated at 100° C. for two minutes, is added to the hybridization solution at 1 to 233 10$^6$ cpm/ml.

The hybridization is performed at 55° C. for at least 1 hour. After hybridization, the filters are washed in the 6×SSC plus 0.1% SDS buffer, once or twice at 65° C. for 20 minutes. The filters are then placed in a cassette equipped with "CRONEX" (DUPONT) intensifiers, placed in contact with a Kodak XAR-5 film for autoradiography for 7 to 36 hours at −70° C.

EXAMPLE 3

Synthesis and Purification of the Synthetic Oligonucleotides of Formulae (12) to (29)

Procedure is as described in Example 1, to prepare DNA fragments of formulae (12) to (29).

EXAMPLE 4

Determination of the Sex of Bovine Embryos by Hybridization in Situ with the Biotinylated DNA Fragments (Non-radioactive) of Formula (1) to (29)

A. Preparation of the cells

The cells used come from bovine embryos aged 7 to 8 days gestation. After having been dissequated, the cells are deposited on a slide and incubated for 10 to 15 minutes in a fixing solution such as the mixture alcohol-acetic acid (3:1 v/v) then dried in air. Slides are used immediately or, in the case of-postponed sexing, stored at 4° C. protected from dust.

B. Biotinylation of the DNA fragments of formulae (1) to (29).

The biotinylation of said fragments is performed by the addition at the 3' end of a biotinylated d UTP or any other biotinylated deoxynucleotide by means of terminal-transferase enzyme (Boehringer) .

10 to 20 pM respectively of the synthetized fragments are added to 100 μl of reactional mixture composed of: 140 mM of potassium cacodylate; 30 mM Tris-HCl pH 7.6; 0.1 mM dithiothreitol; 1 mM CoCl$_2$+0 02 mM of biotinylated dUTP and 1 to 2 units of terminal-transferase enzyme.

After incubation for 1 hour at 37° C., the labelled oligonucleotide is separated by chromatography on a column with superfine Sephadex 25.

C. Technique of Hybridization on slides.

Slides are incubated with 90 to 100 μl of hybridization liquid and coated with a plastic film(to avoid evaporation). After denaturation for 10 mn in an oven at 100° C., the slides are placed in a moist chamber and incubated at 55° C. for 16 hours.

Final composition of the hybridization liquid is:

0.9M NaCl
5 mM EDTA
50 mM NaHPO$_4$ pH 7.4
5 x Denhart
0.5% SDS
(5×Denhart=0.1% BSA, or 0.1% powdered skimmed milk;
0.1% polyvinylpyrrolidone
0.1% Ficoll);

After having removed the plastic film, the slides are washed successively in a 6×SSC solution (2×30 minutes at 55° C.), then in PBS pH 7.4 supplemented with 0. 1% v/v of Triton X−100 and 0.5% (p/v) of powdered skimmed milk (Regilait).

D. Development

The still wet slides after removing the excess fluid are then incubated for 1 hour at 37° C. with a goat antibody antibiotineor with a rabbit antibody anti-biotine. This antibody is sold purified by affinity chromatography (Vector Laboratories ref. SP-3000) and is used in our tests, diluted to 1:350 in PBS pH 7.4+0.1% (v/v) Triton X−100+0.5% (p/v) powdered skimmed milk.

After washing 15 minutes at the room temperature in PBSpH7.4 +0.1% (v/v) Triton X−100+0.5% (p/v) powdered skimmed milk, the slides are then incubated 1 hour at 37° C., with a conventional rabbit anti-goat antibody or anti-rabbit goat coupled with peroxidase (Biosys ref. BI 2403) diluted 1:40 in PBS pH 7.4+Triton 0.1% +0.5% powdered skimmed milk.

The slides are then washed twice for 15 minutes in PBS pH 7.4 containing this time 0.1% (v/v) of Tween-20 and finally in PBS pH 7.4 for 5 minutes.

Incubation for 5 to 8 minutes at room temperature follows with a diaminobenzidine solution (DAB SIGMA ref. D 8001) at 0.5 mg/ml in PBS pH 7.4 containing 0.01% of H$_2$O$_2$.

The precipitate formed by the action of peroxidase on the DAB is amplified by successive precipitations of gold and silver salts by the method described by BURNS et al. (Journal Clinical Pathology 1985, 35, 1085-1092):

In a first stage, 50 to 100 μl per slide of a 2.5 mM solution of mM solution of Na (NaAuCl BDH ref. 30125 2R) Na (NaAuCl BDH ref. 30125 2R) are deposited and they are incubated 5 mn at room temperature. After washing for 5 mn in distilled water, the slides are incubated 5 mn at room temperature with 50 to 100 μl of a 0.1M solution of Na Sulfide (Na$_2$S, SIGMA ref. S 2006), rinsed 5 mn with distilled water and incubated 4 to 8 mn with 100 to 300 μl of silver reagent.

The composition of the silver reagent is as follows:

| | | |
|---|---|---|
| A Na Carbonate | 0.24 M | (SIGMA ref. S 4132) |
| B1 Ammonium Nitrate | 13 mM | (SIGMA ref. A 9642) |
| B2 Silver Nitrate | 6 mM | (BDH ref. 303873N) |
| B3 Dodecatungstosilicic acid | 1.5 mM | (BDH ref. 305453R) |
| B4 Formaldehyde 37% | 0.6 μl/ml | (SIGMA ref. F 1635) |

The silver reagent is prepared by mixing successively and with stirring the solutions B1-B2-B3-B4. The mixture obtained is added 1:1 to the solution A and the reagent thus prepared is used immediately.

After the treatment with the silver reagent, the slides are washed with distilled H$_2$O for 15 minutes, then in acetic acid 1% (v/v) twice for 15 minutes and finally dyed for 1 minute in Pyronin Y (SIGMA ref. P 7017) 1% in H$_2$O, rinsed for some seconds with distilled water, dried in hot air and mounted on DPX.

EXAMPLE 5

Control of the Quality of the sorting of a Bovine Spermatozoa Population with the DNA Probes Specific of the Male Sex According to the Invention Preparation of the cells Cells used are bull spermatozoa frozen and stored in liquid nitrogen. A small flake is thawed, being about 13,000,000 living spermatozoa. The flakes are reheated for 30 seconds at 37° C. and then the sperm diluted in 1 ml of sterile PBS. A series of centrifugations for the purpose of maximum removal of the freezing medium follows. The suspension of spermatozoa in PBS is first centrifuged for 10 mn at 500 g, the supernatant is sucked out and the spermatozoa taken up again in 1 ml of 0.11M sodium citrate. They are centrifuged 10 mn at 500 g. The supernatant is sucked out, and the spermatozoa are again in i ml of 0.11M sodium citrate+5% DMSO, centrifuged 10 mn at 500 g. The supernatant is sucked out, the spermatozoa are resuspended in 1 ml of 0.11M sodium citrate+15% DMSO. They are centrifuged 10 mn at 500 g. The supernatant is sucked out, the spermatozoa resuspended in 1 ml of 0.11M sodium citrate +50% DMSO. They are centrifuged 10 mn at 500 g. The supernatant is sucked out; the spermatozoa are resuspended in 1 ml of 0.11M sodium citrate in Tris-HCl 0.1M pH 7.4 and centrifuged 10 mn at 500 g. The supernatant is sucked out and the spermatozoa resuspended in 250 μl of the same buffer.

At this stage, the cells are either deposited on a slide (30–40 μl of spermatozoa suspension per slide) and treated by hybridization in situ with one of the biotinylated probes of formulae (1) to (29), or deposited on a filter and hybridization by the dot-blot technique with one of the probes of formulae (1) to (29) labelled by means of radio-active nucleotides. EXAMPLE 6

Genic Amplification in Vitro of the Molecular Probes of DNA Specific of the Male Genome of Ruminant Mammals, Particularly of the Bos Genus The genic in vitro amplification process is based on successive cycles—of hybridization of probes with the oligonucleotidic "primers" (the "primers" are flanking segments and, specifically, in the present case, anyone of the fragments of formulae ( 1 ) to (29) ,—extension from the "primers", by means of DNA-polymerase enzyme and—denaturation, for example by a procedure called PCR ("Polymerase chain reaction") described by the CETUS CORPORATION COMPANY (cf. particularly MULLIS et al. , COLD SPRING HARBOR SYMPOSIA ON QUANTITATIVE BIOLOGY, Vol. I-I, 1986, pages 263-272). The cells of a biopsy are deposited in a microtube under a volume of 10 μl in PBS—35 μl of H$_2$O are added, then the tube is placed at 95° C. for 10 minutes to lyse the cells and denature the DNA. In the lysate is added 55 μl of the PCR buffer (50 mM KCl, 10 mM Tris pH 8,3,8 mM MgCl$_2$, 1 μM of primer A to be fixed to one of the ends of the probe, 1 μM of primer B to be fixed to the other end of the probe, 1.5 mM of ATP, 1.5 mM of dCTP, 1.5 mM dTTP, 1.5 mM dGTP. The specimens are then transferred at a suitable temperature for 2 minutes so that the primers are fixed. The extension of the strands is primed by the addition of 4 units of "Taq Polymerase" (CETUS CORPORATION) and incubation at 69° C.

for 2 minutes. This cycle is repeated 30 to 40 times. The samples are then denatured in a solution 0.4N NaOH, 25 mM EDTA and deposited on a nylon membrane manually or by means of a dot-blot apparatus. The repetition of this cycle 30 to 40 times procures an increase of $1 \times 10^{12}$ times the amount of the starting sequence which constitutes the probe proper. The membranes are then neutralized and dried at 80° C., prehybridized and hybridized at 40° or at 65° C. according to the primer employed, in a buffer 5×SSPE, 5×Denhart, 0.5% SDS containing the probes radio-labelled at 5'-end with $X/\gamma^{32}P/ATP$ by means of the polynucleotide-kinase enzyme, Probes (49 mer or 17 mer or 20 mer) may be either radio-active, or labelled with biotine or with another cold compound. The hybridization is carried out from 40° to 60° C. for 1 hour. The membranes are then washed twice in 2×SSPE, 0.1% SDS at room temperature, followed by the washing at 45° C. in the same buffer for 10 minutes. For the radio-active probes, the autoradiography is performed for 30 minutes to 10 hours at −80° C. with an intensifying screen. For the cold probes, the demonstration of the hybridization is done by a sequence of immunocytochemical reactions described in Example 3 above. In the case of a specific example in which the primers A and B are respectively the fragment of formula (7) and the fragment of formula (1):

Amorce A:

   (7)

Amorce B:

   (1)

the PCR cycle progresses in the following manner:

The biopsy cells are deposited in a microtube in a volume of 10 μl in PBS with the addition of 35 μl of H₂O, as described above; however, the tube is placed at 95° C. for only 2 minutes and the operations are continued as described above, except that the samples are transferred for 2 minutes at 55° C. and the incubation with the "Taq Polymerase" takes place at 69° C. for 2 minutes and the cycle is repeated 40 times.

With other primers it will be recommended to perform the incubation with the "Taq Polymerase" at a lower temperature, of the order of 37° C. for example, or to perform the incubation in certain cycles at this temperature, and at 55° C. in other cycles, the durations being opportunely slightly prolongea or reduced according to the primers employed.

The probe employed may be a probe selected from among the probes or fragments of formulae A and 1 to 29. It will be possible, for example, with the primers of formulae (7) and (1) to use a probe of formula (4):

```
    5'                    3'           (4)
    AGATGTGCTCCAAGGAG
```

In such a case, the prehybridization is carried out as well as the hybridization, at 65° C.

With this system, a very intense male signal is obtained, distinct from that of females which is very weak, starting from 125 picograms of DNA, namely the equivalent of 25 cells and directly from cells with 50 male cells, after 30 minutes autoradiography.

In the same manner, by using, for example, as a probe a fragment of formula (2) or formula (3), with the primers respectively of formulae (8) and (5), a specifically male signal is obtained, from 125 picograms of DNA.

Although the foregoing description has essentially taken account of the part played by the probes of formulae (1) to (29), for the determination of the sex of bovine embryos, the checking of the presence of the Y chromosome in a spermatozoa population and the separation of the latter into two groups comprising respectively the Y chromosome and the X chromosome for their use in artificial insemination, easily understood that this role may extend to other animals to the extent that the latter show DNA sequences specific of the male sex similar to those of said bovine embryos; in the same way, the role of probes of formulae (1) to (29) as described in the foregoing, is given purely by way of non-limiting example and may be extended to the research of other specific sequences of the male sex.

Thus as emerges already from the foregoing, the invention is in no way limited to those of these types of performing embodiments and uses which have just been described more explicitly; it encompasses on the contrary all modifications which may come to the spirit of a technician in the art, without departing from the scope, nor of the range of the present invention.

We claim:

1. A synthetic oligonucleotide selected from the group consisting of a 49 base sequence of nucleotides of formula (A) below:

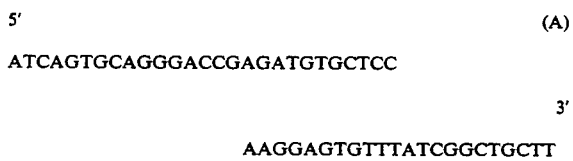

and fragments thereof consisting of 17 or more consecutive bases of sequence A.

2. A synthetic oligonucleotide selected from the group consisting of oligonucleotides having the formulae (1) to (8) below:

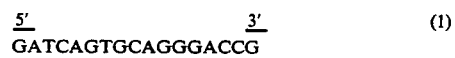   (1)

   (2)

   (3)

   (4)

   (5)

   (6)

   (7)

   (8)

as well as oligonucleotides that are 17 bases long and fully complementary.

3. A synthetic oligonucleotide selected from the group consisting of oligonucleotides having the formulae (9) to (11) below:

$$\underline{5'}\text{ATCAGTGCAGGGACCGAGAT}\underline{3'} \quad (9)$$

$$\underline{5'}\text{GTGCTCCAAGGAGTGTTTAT}\underline{3'} \quad (10)$$

$$\underline{5'}\text{GGACCGAGATGTGCTCCAAG}\underline{3'} \quad (11)$$

as well as oligonucleotides that are 20 bases long and fully complementary.

4. A process for the amplification of DNA sequences specific to the male genome of the Bos genus, comprising performing a polymerase chain reaction amplification using as primers selected from the synthetic oligonucleotides according to claims 1, 2 or 3.

5. A process for the determination of the sex of embryos or of foeti of ruminant mammals, of the Bos genus comprising: detecting a DNA sequence specific for the male genome by hybridization with a synthetic oligonucleotide according to claims 1, 2 or 3 which has been labelled by a radioisotope or by a non-radioactive substance.

6. A process for determining the presence of the Y chromosome in a spermatozoid population of ruminant mammals of the Bos genus, comprising:

detecting a DNA sequence specific for the male genome by hybridization with a synthetic oligonucleotide according to claims 1, 2 or 3 which has been labelled by a radioisotope or by a non-radioactive substance.

* * * * *